United States Patent [19] [11] Patent Number: 4,994,029
Rohrbough [45] Date of Patent: Feb. 19, 1991

[54] SYRINGE MIXER AND INJECTOR DEVICE

[75] Inventor: John Rohrbough, Walnut, Calif.

[73] Assignee: David Bull Laboratories Pty. Ltd., Mulgrave, Australia

[21] Appl. No.: 405,989

[22] Filed: Sep. 12, 1989

[51] Int. Cl.[5] .......................................... A61M 37/00
[52] U.S. Cl. ..................................... 604/88; 206/222; 215/DIG. 8; 222/82
[58] Field of Search ........................... 604/82-88, 604/56, 416, 411; 222/82, 83, 83.5, 89, 91, 135, 136; 215/DIG. 8; 206/222

[56] References Cited

U.S. PATENT DOCUMENTS

| 2,490,552 | 12/1949 | Smith | 604/88 |
|---|---|---|---|
| 3,314,429 | 4/1967 | Boehm et al. | 222/83 X |
| 3,397,694 | 8/1968 | Ogle | 604/88 |
| 3,542,023 | 11/1970 | Ogle | 604/88 |
| 3,547,122 | 12/1970 | Rinser | 604/88 |
| 3,563,373 | 2/1971 | Paulson | 206/229 |
| 3,570,486 | 3/1971 | Engelsher et al. | 604/88 |
| 3,659,602 | 5/1972 | Cloyd | 604/88 |
| 3,730,392 | 5/1973 | Marancl | 222/82 |
| 3,987,791 | 10/1976 | Chittenden et al. | 222/83 X |
| 3,995,630 | 12/1976 | van de Veerdonk | 604/416 X |
| 4,146,153 | 3/1979 | Bailen | 222/83 |
| 4,346,820 | 8/1982 | Cavazza | 222/83 |
| 4,516,967 | 5/1985 | Kopfer | 604/87 |
| 4,607,671 | 8/1986 | Aalto et al. | 141/329 |
| 4,614,437 | 9/1986 | Buehler | 604/88 X |
| 4,619,651 | 10/1986 | Kopfer et al. | 604/415 |
| 4,648,532 | 3/1987 | Green | 222/82 |
| 4,743,229 | 5/1988 | Chu | 604/82 |
| 4,759,756 | 7/1988 | Forman et al. | 604/413 |
| 4,850,978 | 7/1989 | Dudar et al. | 604/201 |
| 4,861,335 | 8/1989 | Reynolds | 604/88 |
| 4,886,495 | 12/1989 | Reynolds | 604/88 |

Primary Examiner—John D. Yasko
Assistant Examiner—Adam J. Cermak
Attorney, Agent, or Firm—Darby & Darby

[57] ABSTRACT

Syringe mixer and injector device formed of an injector and an adaptor having opposed interconnectable nozzles, e.g. with mating luer lock connectors, on their facing ends and sockets in their remote ends. Each of the injector and adapter has a protected fluid pathway flow connecting its nozzle and socket, a guideway to receive at its remote end for movement thereon a medicament vial when the vial stopper is connected to its socket, and a recessed short tubular spike forming the pathway portion in its socket and protruding into the socket and terminating inwardly from its remote end sufficiently to protect the spike from unintended human contact and arranged to penetrate the stopper thereat to flow connect its vial with its pathway in protected condition. After charging the injector connected vial with the contents of the adapter connected vial, e.g. by one-way transfer thereto, the injector nozzle may be disconnected from the adapter nozzle and connected directly without modification to a dispensing device having a like nozzle to that of the adaptor. Each of the injector and adapter may be made of plastic as an integral one-piece member.

8 Claims, 2 Drawing Sheets

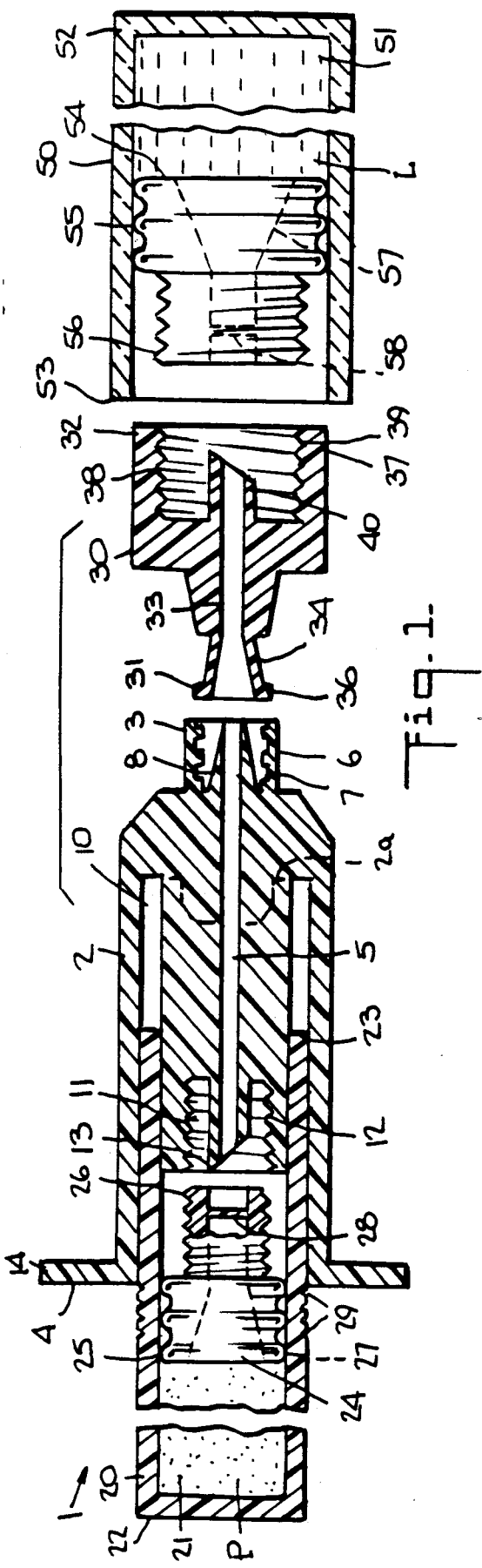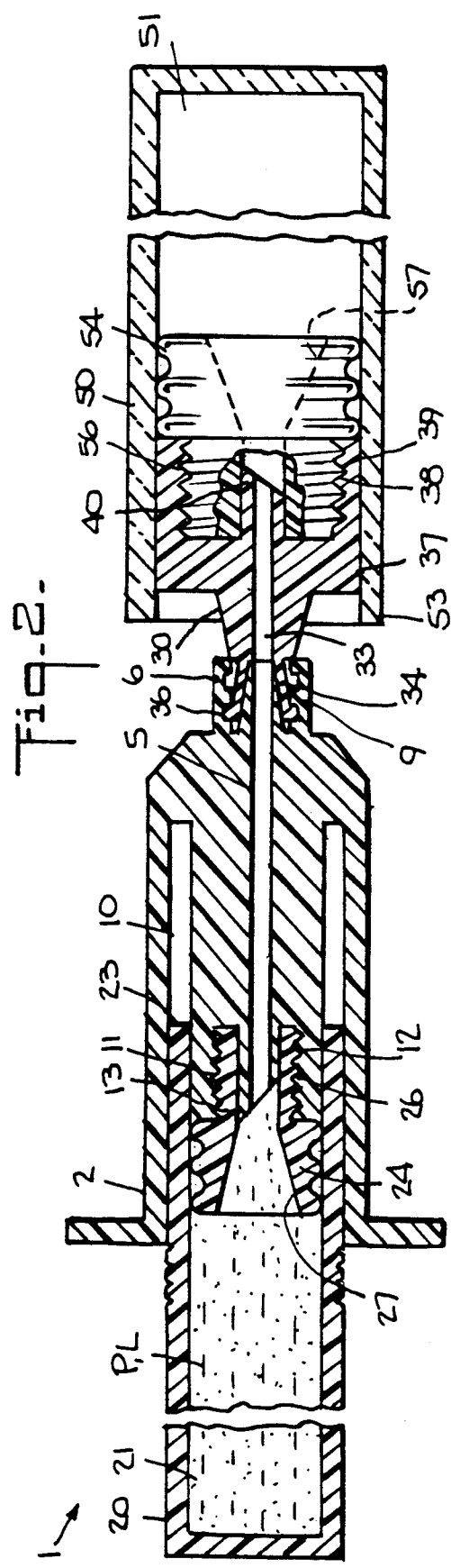

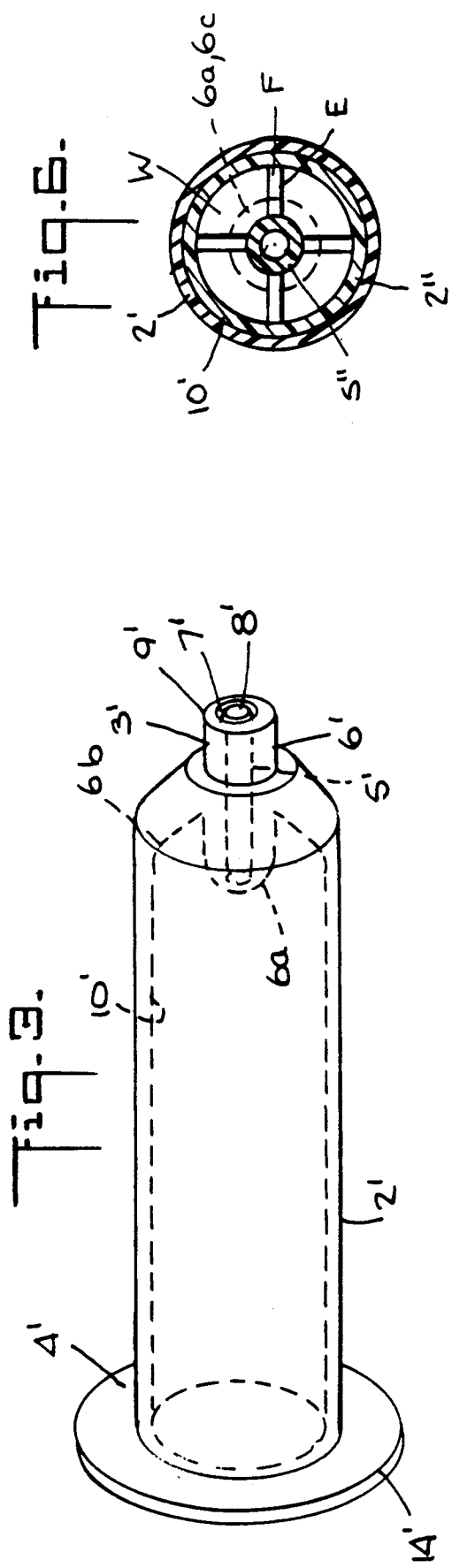
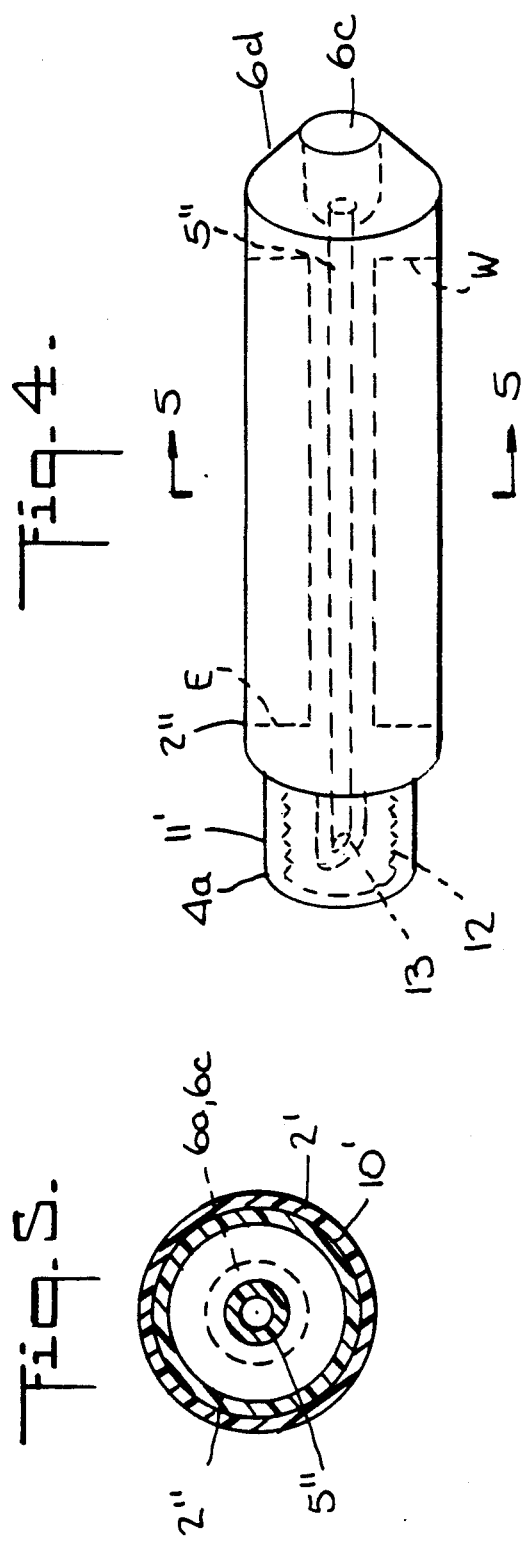
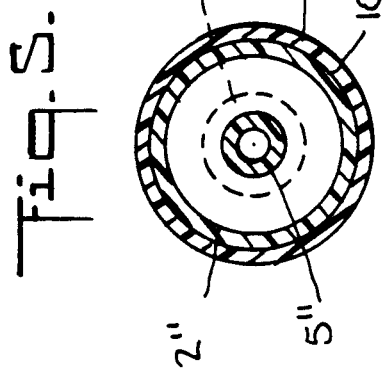

SYRINGE MIXER AND INJECTOR DEVICE

FIELD AND BACKGROUND OF THE INVENTION

The present invention relates to a syringe mixer and injector device, and more particularly to such a device including an injector and an adapter having opposed interconnectable nozzles on their facing ends and sockets in their remote ends flow connected by corresponding protected fluid pathways, and a recessed short tubular spike in each socket to penetrate the stopper of a vial connected to that socket, to charge the injector connected vial with the contents of the adapter connected vial, e.g. by one-way transfer thereto, then disconnect the injector nozzle from the adapter nozzle and connect it directly and without modification to a dispensing device having a like nozzle to that of the adapter.

U.S. Pat. No. 2,490,552 to Smith shows a syringe having an axially shiftable single hollow needle with opposed pointed ends arranged to permit the user to push the exposed pointed end inwardly until the internal pointed end punctures a seal to flow connect the needle with a prefilled medicament chamber, to prepare the syringe for use, but disadvantageously in slow and cumbersome manner, and at risk of accidental skin puncture or other injury to the user when pushing the exposed needle end inwardly against the seal, as well as at risk of contamination of the medicaments, the user and the environment.

U.S. Pat. No. 3,897,694 to Ogle shows a medicament powder charged syringe having a single hollow needle, with its inner end separated from the powder by a stopper, and its outer pointed end in the neck of a medicament liquid charged, ram containing, vial having a plug facing the pointed needle end, enabling the liquid to be forced by the ram against the plug until punctured by the needle, and then pass through the needle to unseat the stopper and mix with the powder, followed by vial removal for use of the syringe. Instead of a needle, the syringe and vial may have luer lock connections, with the vial using a bypass plug to enable the liquid to reach the powder when forced by the ram, the syringe then being used with a dispensing needle having a corresponding luer lock connection.

Disadvantageously, the constructions of this Ogle patent are complicated, expensive, require many different and precisely interfitting parts, and must be used with a special type liquid charged vial, and thus must withstand without leakage the internal hydraulic pressures generated in operating the vial ram to effect transfer of the liquid to the syringe.

U.S. Pat. No. 4,516,967 to Kopfer shows a medicament liquid charged syringe. Whose needle is pushed to puncture the seal of a medicament powder charged vial, whereupon the liquid is forced from the syringe into the vial to mix with the powder and then the admixture is withdrawn back into the syringe, disadvantageously requiring slow and cumbersome two-way liquid transfer to achieve mixing and syringe preparation.

U.S. Pat. No. 4,619,651 to Kopfer et al shows a syringe transfer system similar to the above Ogle and Kopfer patents but in this case the syringe, whose needle is attached by a luer lock connection, is used with a special type vial whose neck has a double seal forming an intermediate holding chamber.

U.S. Pat. No. 3,542,023 to Ogle; U.S Pat. No. 8,547,122 to Rinser etal; U.S. Pat. No. 3,563,373 to Paulson; and U.S. Pat. No. 3,570,486 to Engelsher et al variously show analogous syringes having a single long hollow needle with opposed pointed ends arranged for charging the syringe upon puncturing the seal of an associated vial via a given pointed end of the needle.

U.S. Pat. No. 4,648,532 to Green shows a powder charged dental preparation capsule having a front nozzle and a rear ram, and containing a liquid filled pillow inwardly of the nozzle, such that on pushing a rod into the nozzle to puncture the pillow, the released liquid admixes with the powder, enabling the ram to force the admixture out through the nozzle.

It would be desirable to provide a syringe mixer and injector device of detachable parts for transfer of a medicament liquid from a charging vial to a medicament solid or liquid in a receiving vial for admixture therein without retransfer to the charging vial, yet easily and rapidly, under safe and sterile conditions, and permitting the part associated with the filled receiving vial to be detached and connected directly and without modification to a dispensing device.

SUMMARY OF THE INVENTION

It is among the objects of the invention to provide a syringe mixer and injector device formed of an injector and an adapter having opposed interconnectable nozzles on their facing ends and sockets in their remote ends flow connected by corresponding protected fluid pathways, and a recessed short tubular spike in each socket to penetrate the stopper of a vial when connected to that socket, to charge the injector connected vial with the contents of the adapter connected vial, then disconnect the injector nozzle from the adapter nozzle and connect it directly and without modification to a dispensing device having a like connectable nozzle to that of the adapter.

It is among the additional objects of the invention to provide such a device which can be used with a receiving vial charged with a medicament solid or liquid, and a charging vial charged with a medicament liquid for one-way transfer to the receiving vial for admixing the medicaments therein without retransfer to the charging vial, and without risk of accidental skin puncture or other injury to the user from any exposed needles, or of contamination of the medicaments, the user or the environment.

It is among the further objects of the invention to provide such a device for administering quickly and safely a preset dosage of two separate medicaments readily combined at the time of use, under improved conditions of sterility, and providable in a compact, storable form, and which can be fabricated from conventional materials and components in simple and inexpensive manner.

According to this invention, a syringe mixer and injector device is provided which comprises an injector and an adapter, each having an inner end and an outer end and a protected fluid pathway extending longitudinally therethrough from the inner end to the outer end thereof.

The injector inner end has a connection nozzle defining the inner terminus of its pathway and the adapter inner end has a counterpart connection nozzle defining the inner terminus of its pathway, the nozzle and counterpart nozzle being arranged to interconnect releasably the injector and adapter to flow connect their pathways in protected fluid tight condition.

Each of the injector and adapter has a guideway extending from the outer end toward the inner end thereof, adapted to receive and guide for movement longitudinally relative thereto a respective medicament containing vial having an open end closed by a penetrable stopper movable longitudinally along the vial relative to its open end.

Each of the injector and adapter also has a connecting socket defined in the outer end thereof, adapted to connect stationarily the corresponding stopper thereat, and a tubular spike defining the outer terminus of the pathway thereof and protruding into the respective socket and terminating inwardly from the respective outer end sufficiently to protect the spike from unintended human contact and arranged to penetrate the corresponding stopper to flow connect its vial with the respective pathway in protected fluid tight condition.

Desirably, the nozzle and counterpart nozzle have mating luer lock connection formations to interconnect releasably the injector and adapter.

In particular, each socket defines an axial cylindrical recess and each spike defines an axial hollow cylindrical tubular portion centrally arranged coaxially with its respective recess. Each spike favorably is cantilevered and has a pointed free end and a base end which is integral with the adjacent portion of the corresponding end of the injector and adapter through which the respective pathway extends. Also, each socket preferably has an internal thread connection formation adapted to mate with a counterpart external thread connection formation on the stopper of a corresponding vial to be connected thereto. The injector and adapter may be formed of plastic, each as an, e.g. injection molded, integrally connected one-piece member.

BRIEF DESCRIPTION OF THE DRAWINGS

Other objects of the invention will become apparent from the within specification and accompanying drawings, in which:

FIG. 1 is a schematic exploded view of a syringe mixer and injector device according to an embodiment of the invention, showing the injector and adapter, each associated with a medicament containing vial;

FIG. 2 is a schematic view of the device of FIG. 1, showing the injector and adapter connected to each other and to their associated medicament containing vials for charging the contents of the adapter associated vial via the adapter and injector to the injector associated vial;

FIGS. 3 and 4 are schematic views of an exterior injector part and an interior injector part, respectively, readily joined together to form a one-piece injector similar to that shown in FIG. 1:

FIG. 5 is a schematic sectional view taken along the line 5—5 of FIG. 4; and

FIG. 6 is a sectional view similar to FIG. 5 showing a modified form of the internal injector part of FIG. 4.

DESCRIPTION OF THE PREFERRED EMBODIMENTS

Referring to the drawings, and initially to FIG. 1, a syringe mixer and injector device 1 is shown, including an injector 2 and an adapter 30, plus an associated medicament powder or liquid containing receiving vial in the form of a plunger vial 20 for injector 2 and an associated medicament liquid containing charging vial 50 for adapter 30.

Injector 2 has an inner end 3 and an outer end 4, and a protected, e.g. central, fluid pathway 5 extending longitudinally therethrough from inner end 3 to outer end 4.

Injector inner end 3 has a connection nozzle 6, provided with a nozzle recess 7 containing a tapered, e.g. central, spout 8 defining the inner terminus of pathway 5 and a lock connection formation, such as a luer lock tab 9, arranged to form a male connection formation for interconnecting releasably with mating parts on adapter 30 to flow connect their pathways in protected fluid tight condition, as noted below.

Injector outer end 4 has a guideway 10 extending therefrom toward inner end e.g. formed as an internal recess of annular or hollow cylindrical shape, to receive and guide, e.g. coaxially, plunger vial 20 for movement both longitudinally and rotationally relative thereto. Outer end 4 also has a connecting socket 11 defined therein and provided with internal threads 12, plus a relatively short, e.g. central, tubular spike 13 defining the outer terminus of pathway 5 and protruding, e.g. coaxially, into socket 11 and terminating inwardly from outer end 4 sufficiently to protect spike 13 from unintended human contact at socket 11. Lateral flanges 14 may be formed on outer end 4 as user finger grips.

The injector associated plunger vial 20 may be of conventional type, e.g. a cylindrical member having a chamber 21 charged with a preset dosage of a medicament liquid or solid P, e.g. a powder, a closed rear end 22 and an open front end 23 sealed by a shiftable internal cylindrical stopper 24. Stopper 24 has external seal rings 25 on its main diameter body portion engaging the interior surface of chamber 21, and external threads 26, e.g. coaxially, on its reduced diameter cylindrical tip portion spaced inwardly from the interior surface of chamber 21, plus an internal, e.g. central, bore 27 containing a penetrable seal 28 adjacent the forwardmost portion of its tip (shown in phantom in FIG. 1).

The exterior of plunger vial 20 may contain score line graduations 29 to define dosage volume or other indicia.

Plunger vial 20 and guideway are sized and, e.g. coaxially, arranged for mating coaction to permit open end 23 of cylindrical plunger vial 20 to be inserted slidably, e.g. coaxially, into the counterpart recess of guideway 10 at injector outer end 4 for longitudinal reciprocation as well as rotation of plunger vial 20 on injector 2. Also, stopper 24 and socket 11 are sized and, e.g. coaxially, arranged for mating coaction to permit external threads 26 on the tip of stopper 24 to be screwed onto internal threads 12 in socket 11 sufficiently for spike 13 to penetrate seal 28, e.g. coaxially, and flow connect pathway 5 and chamber 21 in protected fluid tight condition, as plunger vial 20 is rotated relative to injector 2 (FIG. 2).

Thus, stopper 24 will be stationarily connected by its threads 26 to threads 12 of socket 11, yet by reason of its shiftable disposition in chamber 21, reciprocation of plunger vial 20 will cause stopper 24 to move longitudinally therealong relative to open end 28. Since plunger vial 20 initially contains a relatively small volume charge of medicament P, stopper 24 will normally be initially located in recessed position remote from open end 23, such that plunger vial 20 may be inserted in guideway 10 without spike 13 penetrating seal 28 in bore 27 of stopper 24 (FIG. 1).

Likewise, adapter 30 has an inner end 31 and an outer end 32, and a protected, e.g. central, fluid pathway 33 extending longitudinally therethrough from inner end 31 to outer end 32.

Adapter inner end 31 has a counterpart connection nozzle 34, provided with a tapered, e.g. central, recess or entry 35 defining the inner terminus of pathway 33 and a lock connection formation, such as a luer lock tab 36, arranged to form a female connection formation for interconnecting releasably with the male connection formation formed by spout 8 and luer lock tab 9 in recess 7 of injector nozzle 6, e.g. coaxially therewith, to flow connect pathways 5 and 33 in protected fluid tight condition and entirely free of dead spaces (FIG. 2).

Adapter outer end 32 has its own guideway 37 extending therefrom toward inner end 31, e.g formed as a cylindrical, e.g. coaxial, outer surface thereof, to receive and guide, e.g. coaxially, charging vial 50 for movement both longitudinally and rotationally relative thereto. Outer end 32 also has its own connecting socket 38 defined therein and provided with internal threads 39, plus a relatively short, e.g. central, tubular spike 40 defining the outer terminus of pathway 33 and protruding, e.g. coaxially, into socket 38 and terminating inwardly from outer end 32 sufficiently to protect spike 40 from unintended human contact at socket 38.

The adapter associated charging vial 50 may likewise be of conventional type, e.g. a cylindrical member having a chamber 51 charged with a preset dosage of a medicament liquid L, a closed rear end 52 and an open front end 53, sealed by a shiftable internal cylindrical stopper 54 having external seal rings on its main diameter body portion engaging the interior surface of chamber 52, and external threads 56, e.g. coaxially, on its reduced diameter cylindrical tip portion spaced inwardly from the interior surface of chamber 51, plus an internal, e.g. central, bore 57 containing a penetrable seal 58 adjacent the forwardmost portion of its tip (shown in phantom in FIG. 1).

Charging vial 50 and guideway 37 are likewise sized and, e.g. coaxially, arranged for mating coaction to permit open end 53 of cylindrical charging vial 50 to be inserted slidably, e.g. coaxially, onto the counterpart surface forming guideway 37 at adapter outer end 32 for longitudinal reciprocation as well as rotation of charging vial 50 on adapter 30. Also, stopper 54 and socket are sized and, e.g. coaxially, arranged for mating coaction to permit external threads 56 on the tip of stopper 54 to be screwed onto internal threads 39 in socket 38 sufficiently for spike 40 to penetrate, e.g. coaxially, seal 58 and flow connect pathway 33 and chamber 51 in protected fluid tight condition, as charging vial 50 is rotated relative to adapter 30 (FIG. 2).

Likewise, stopper 54 will be stationarily connected by its threads 56 to threads 39 of socket 38, Yet by reason of its shiftable disposition in chamber 51, reciprocation of charging vial 50 will cause stopper 54 to move longitudinally therealong relative to open end 53. Since charging vial 50 initially contains a relatively large volume charge of medicament liquid L, stopper 54 will normally be initially located adjacent open end 53, such that more or less immediately upon inserting charging vial 50 onto guideway 37, spike 40 can penetrate seal 58 in bore 57 of stopper 54 (FIG. 1).

Desirably, in injector 2 and adapter 30, respectively each socket 11,38 defines an axial cylindrical recess and each short spike 13,40 defines an axial hollow cylindrical tubular portion centrally arranged coaxially with its respective recess. Also, each spike 13,40 is cantilevered and has a pointed free end and a base end which is integral with the adjacent portion of the corresponding end of injector 2 and adapter 30 through which the respective pathway 5,33 extends.

Thus, when counterpart nozzle 34 of adapter 30 is connected to nozzle 6, and plunger vial 20 is mounted on guideway 10 of injector 2 and charging vial 50 is mounted on guideway 37 of adapter 30, charging vial 50 may be rotated to screw stopper 54 into socket 38 to cause spike 40 to penetrate seal 58, and then plunger vial 20 may be rotated to screw stopper 24 into socket 11 to cause spike 13 to penetrate seal 28, whereby to achieve tandem flow connection of plug bore 57, pathway 33, pathway 5 and plug bore 27 in protected fluid tight condition, and form a continuous, yet separable, interior fluid conduit system between the vials, entirely free of dead spaces.

Then, charging vial 50 may be pushed towards adapter 30 to transfer liquid L from chamber 51 through plug bore 57, pathways 33 and 5, and plug bore 27 into chamber 21, thereby causing plunger vial 20 to be retracted outwardly from injector 2 as liquid L fills chamber 21 and admixes with solid or liquid P already present therein (FIG. 2). These attached components 20,2,30,50 may be manually shaken, if needed, to assure complete admixing of medicaments P.L in plunger vial 20, but the basic procedure of combining medicaments P.L is achieved by a one-way, one-step transfer of liquid L from vial 50 to vial 20 through adapter 80 and injector 2, without any retransfer of the combined medicaments P,L back to vial 50.

Thereafter, adapter 30 (and vial 50) may be detached from injector 2 (and vial 20) and a separate standard dispensing device, having a tapered entry and luer lock tab, like tapered entry 35 and luer lock tab 36 of adapter 80, i.e. forming a female connection formation counterpart to the male connection formation on injector nozzle 6, may be immediately and directly attached to nozzle without intervening modification, enabling injector 2, carrying plunger vial 20 (now filled with the desired preset dosage volume of admixed medicaments P,L) on outer end 4, and the attached dispensing device on inner end 3, to be used forthwith to dispense the admixed medicaments.

The separate standard dispensing device may be for instance a three-way stopcock or protected needle for injection into a latex resealable I.V. injection port of an intravenous injection unit, or the like, or any other dispensing device, e.g. for non-injectable use of the medicament mixture, having a mating connection formation to that of injector nozzle 6, such as a mating luer lock connection formation as described above.

These luer lock formations permit easy and rapid connection and release onto injector nozzle 6 of counterpart nozzle 34 of adapter 30 and the corresponding connection formation of the separate dispensing device, and may be of standard size. These luer lock connection formations are easily and rapidly connected and disconnected, e.g. by twisting clockwise to connect them and counterclockwise to disconnect them.

Parenthetically, a certain commercially available medicament mixing and transfer syringe unit utilizes, in conjunction with other components, an injector element having a permanently attached sharp pointed exposed needle, such that once slow and cumbersome transfer and retransfer steps have been undertaken to achieve mixing, disadvantageously the user must take extra time and care to bend back and forth the exposed needle until it snaps off, thereby subjecting the user to the danger of cutting a finger on the sharp bevel portion of the needle, before a separate dispensing device can be attached thereto for dispensing the admixed medicaments.

On the other hand, spikes 13,40 need only be sufficiently long to penetrate vial seals 28,58 to communicate pathways 5,33 with vial chambers 21,51. Thus, they are advantageously recessed a pronounced distance from the entrance to sockets 11,38 and in turn from outer ends 4,32, to protect these relatively short spikes 13,40 from unintended human contact, yet permit easy and rapid penetration of seals 28,58 by mere twisting of vials 20,50 relative to injector 2 and adapter 30.

All portions of injector 2 and adapter 30, respectively including nozzles 6,34 and their luer lock connection formations, and particularly pathways 5,33 and their spikes 13,32, may be made of suitable rigid plastic such as polycarbonate, e.g. by injection molding technique, especially with each spike being integrally interconnected to the adjacent interior socket portion of the injector and adapter defining the interior protected pathway 5,33 therein, e.g. molded-in-place as cantilevered short tubular structures thereon and in recessed relation to the socket opening, so as to form a one-piece member injector 2 and adapter 30.

However, while the structural portions defining nozzles 6,34 may be formed of injection molded parts integral with the remainder of the respective injector 2 and adapter 30, optionally the structural portions defining these respective nozzles 6,34 may be provided as separate such parts, e.g. of a common standard size, and then mounted on and connected, e.g. by sonic welding technique, to the remainder of the respective injector 2 and adapter 30, which may be of any appropriate size, among a number of different sizes, depending on the medicament volume dosage to be admixed and administered, yet fashioned to accommodate the common standard size nozzle 6,34 thereon.

Also, injector 2 may conveniently be made of two separate parts, e.g. by injection molding, and then be integrally interconnected, such as by sonic welding at weld site 2a as shown in phantom in FIG. 1.

In particular, as shown in the modified bipartite injector embodiment of FIGS. 3–5, wherein corresponding parts to those of the injector embodiment of FIG. 1 are assigned the same reference numbers with prime (') or double prime (") designations, as the case may be, the injector may be formed of a separate generally hollow exterior injector part 2' (FIG. 3) and a separate interior injector part 2" (FIG. 4).

As shown in FIG. 3, the inner wall of exterior injector part 2' forms its guideway 10' extending from its outer end 4' toward its inner end 3' carrying the nozzle 6' with its parts 7',8',9' of like construction to those of injector 2. However, injector 2' has a rear nozzle extension 6a protruding rearwardly from a rear abutment wall 6b at inner end 3' containing the inner end pathway portion 5' communicating with nozzle 6'.

On the other hand, as shown in FIG. 4, aside from an optionally reduced diameter outer end 4a, containing its socket 11' provided with threads 12' and recessed spike 13', interior injector part 2" has a front nozzle extension receiving socket 6c in its inner end front nose 6d communicating with its pathway portion 5".

Nose 6d and socket 6c of interior injector part 2" are sized and arranged to mate with abutment wall 6b and nozzle extension 6a of exterior injector part 2' upon inserting interior injector part 2" through the open rear end of hollow exterior injector part 2', such that these parts may be individually formed, e.g. by injection molding, and then be interconnected in one step to form a one-piece integral member, such as by sonic welding between recess 6c and extension 6a, to flow connect pathway portion 6" with pathway portion 5' in fluid tight condition and entirely free of dead spaces (cf. weld 2a in FIG. 1).

FIG. 5 illustrates in cross section the relationship of interior injector part 2" to exterior injector part 2' (shown in phantom) after such interconnection.

Optionally, interior injector part 2" may contain excavated sectors E (shown in phantom in FIG. 4) to conserve material and lighten the structure without detracting from the robust structural integrity of part 2". This modified form is shown more clearly in FIG. 6, with the longitudinally extending four radial fins F defining the boundaries of the excavated sectors E along with the front sector wall W and a similar such wall (not shown) provided adjacent socket 11' (cf. FIG. 4) but spaced therefrom sufficiently to assure that recessed spike 13' will be adequately supported thereat.

Significantly, no portion of spikes 13,40, or spike 13', need be made of metal, which is important in the case of plastic short pointed spikes in that while they will be sufficiently pointed to achieve easy and rapid penetration of standard rubber or like material stoppers on the vials, they will not be so sharp as to present a danger of puncturing the skin of the user.

Moreover, in fabricating the plastic spikes, there is no need to undergo the trouble and expense of providing separate metal needles for incorporation into the injector and adapter and for interconnecting the other portions of the injector and adapter thereto, e.g. by staking technique, nor of cutting or grinding the metal needle outer ends to form them into sharp pointed ends to penetrate the vial stoppers, and then cleansing the needles to remove undesired metal particulates generated during the cutting or grinding, before such staking.

Also, since the short plastic spikes are formable integrally with the adjacent portions of the injector and adapter, they will be much sturdier and more precisely centered in their sockets, e.g. to tolerances controlled by the injection molding process, for more accurate coaxial alignment with the stopper bores of the vials to achieve easy, rapid and safe attachment of the stoppers to the sockets without misalignment of the spikes and stopper bores.

In contrast thereto, a syringe unit having a metal needle is subject to the risk of the needle not being assembled in the construction in perfectly centered alignment for engaging the stopper bore of the associated medicament vial, whereupon the needle may not find the center of the stopper when screwed into the socket of the syringe unit containing the misaligned needle. Once off center, as the vial stopper is rotated into the socket, the needle will bury itself into the thick sidewall of the stopper and not flow connect with the vial contents, thereby rendering the syringe unit inoperable, a result to be avoided in attempting an emergency injection. Use of extra force to achieve flow connection raises the further risk of shattering the vial and injuring the user's hand.

When the injector and adapter of device i are interconnected, these short spikes will form single pointed free end cantilevered tubular extensions in their sockets facing in opposite directions, firmly supported, e.g. molded, at their base ends to the remainder of the injector and adapter and permanently housed entirely within the confines of the surrounding barrel formed by the corresponding outer end of the injector and adapter defining the given socket.

Vials 20,50 may be of standard known type, with vial 50 being charged with a preset dosage of a liquid, e.g. sterile water, as medicament L, and vial 20 being charged with a preset dosage of either another liquid or a solid, such as a particulate powder or tablet, etc., e.g. an emergency drug required to be administered during cardiac arrest, quickly, safely and under sterile conditions, as medicament P compatible with, e.g. dissolvable in, medicament L of vial 50.

Hence, device 1 may be used as a manually operated liquid-liquid (wet-wet) or liquid-solid (wet-dry powder) two compartment mixing and injecting system achieving all the above noted objects. It is especially useful for combining the medicaments by one-way transfer from the charging vial to the plunger vial without retransfer to the charging vial, instead attaining mixing only in the plunger vial, e.g. by mere manual agitation.

The injector and adapter, and the associated vials may be compactly prepackaged as disposable, one-time use, sterile items, e.g. as an emergency kit, with the injector and adapter connected as a preassembled unit having removable protective caps (not shown) on their outer ends, with similar caps being provided on the open ends of the two vials.

This permits the steps of opening the package, removing the caps, pushing the vials onto the injector and adapter for transfer and mixing, detaching the filled plunger vial and injector from the adapter and charging vial, and attaching the standard dispensing device, all to be effected easily and rapidly, without danger to the user from contact with toxic or hazardous medicaments or substances or exposed needle points, or the need to modify the injector to accommodate the standard dispensing device, and at minimum risk of contaminating the sterile medicaments or the environment.

The one-way, one-step transfer and mixing system contemplated by device 1 is thus safer to use than conventional systems, since transfer and mixing are achieved in a completely closed two compartment arrangement, in which from start to finish the user is never exposed to an unprotected needle, let alone required to bend the needle to snap it off from the injector to permit attachment of a separate dispensing device.

The hazard of cuts from working with a device having an exposed needle has become even more dangerous in terms of increased exposure in present day hospital and home care environments to contaminating substances such as those related to HIV (Human Immunodeficiency Virus) and AIDS (Acquired Immune Deficiency Syndrome).

It will be appreciated that the foregoing specification and accompanying drawings are set forth by way of illustration and not limitation of the present invention, and that various modifications and changes may be made therein without departing from the spirit and scope of the present invention which is to be limited solely by the scope of the appended claims.

What is claimed is:

1. Syringe mixer and injector device comprising
    an injector and an adapter, each having an inner end and an outer end and a protected fluid pathway extending longitudinally therethrough from the inner end to the outer end thereof,
    the injector inner end having a connection nozzle defining the inner terminus of the injector pathway and the adapter inner end having a counterpart connection nozzle defining the inner terminus of the adapter pathway, the nozzle and counterpart nozzle having mating lock connection formations arranged to interconnect releasably the injector and adapter to flow connect their pathways in protected fluid tight condition,
    the injector and adapter each having a guideway extending from the outer end toward the inner end thereof, adapted to receive and guide for movement longitudinally relative thereto a respective medicament containing vial having an open end closed by a penetrable stopper movable longitudinally along the vial relative to its open end, and
    the injector and adapter each having a connecting socket defined in the outer end thereof, adapted to connect stationarily the corresponding stopper thereat, and a tubular spike defining the outer terminus of the pathway thereof and protruding into the respective socket and terminating inwardly from the respective outer end sufficiently to protect the spike from unintended human contact and arranged to penetrate the corresponding stopper to flow connect its vial with the respective pathway in protected fluid tight condition.

2. Device of claim 1 wherein each socket defines an axial cylindrical recess and each spike defines an axial hollow cylindrical tubular portion centrally arranged coaxially with its respective recess.

3. Device of claim 2 wherein each spike is cantilevered and has a pointed free end and a base end which is integral with the adjacent portion of the corresponding end of the injector and adapter through which the respective pathway extends.

4. Device of claim 1 wherein the injector and adapter are formed of plastic.

5. Device of claim 4 wherein the injector and adapter are each respectively formed as a separate injection molded, integrally connected one-piece member.

6. Device of claim 5 wherein the injector includes a generally hollow exterior part having an open outer end and an inner end containing the connection nozzle and further containing an inner end portion of the pathway, the inner terminus of the pathway being defined by the connection nozzle, and the injector further includes an interior part having an outer end containing the socket and being provided with the remaining portion of the pathway, the interior part being disposed in the exterior part and being welded thereto whereby to flow connect the inner end portion of the pathway with the remaining portion thereof in fluid tight condition.

7. Syringe mixer and injector device comprising
    an injector and an adapter, each having an inner end and an outer end and a protected fluid pathway extending longitudinally therethrough from the iner end to the outer end thereof,
    the injector inner end having a connection nozzle defining the inner terminus of the injector pathway and the adapter inner end having a counterpart connection nozzle defining the inner terminus of the adapter pathway, the nozzle and counterpart nozzle having mating luer lock connection formations arranged to interconnect releasably the injector and adapter to flow connect their pathways in protected fluid tight condition, the injector and adapter each having a guideway extending from the outer end toward the inner end thereof, adapted to receive and guide for movement longitudinally relative thereto a respective medicament containing vial having an open and closed by a penetrable stopper movable longitudinally along the vial relative to its open end, and the injector and adapter each having a connecting socket defined in the outer end thereof, adapted to connect stationarily the corresponding stopper thereat, and a tubular spike defining the outer terminus of the pathway thereof and protruding into the respective socket and terminating inwardly from the respective outer end sufficiently to protect the spike from unintended human contact and arranged to penetrate the corresponding stopper to flow connect its vial with the respective pathway in protected fluid tight condition.

8. Syringe mixer and injector device comprising an injector and an adapter, each having an inner end and an outer end and a protected fluid pathway extending longitudinally therethrough from the inner end to the outer end thereof, the injector inner end having a connection nozzle defining the inner terminus of the injector pathway and the adapter inner end having a counterpart connection nozzle defining the inner terminus of the adapter pathway, the nozzle and counterpart nozzle being arranged to interconnect releasably the injector and adapter to flow connect their pathways in protected fluid tight condition, the injector and adapter each having a guideway extending from the outer end toward the inner end thereof, adapted to receive and guide for movement longitudinally relative thereto a respective medicament containing vial having an open end closed by a penetrable stopper movable longitudinally along the vial relative to its open end, and the injector and adapter each having a connecting socket defined in the outer end thereof, adapted to connect stationarily the corresponding stopper thereat, and a tubular spike defining the outer terminus of the pathway thereof and protruding into the respective socket and terminating inwardly from the respective outer end sufficiently to protect the spike from unintended human contact and arranged to penetrate the corresponding stopper to flow connect its vial with the respective pathway in protected fluid tight condition, each socket defining an axial cylindrical recess and each spike defining an axial hollow cylindrical tubular portion centrally arranged coaxially with its respective recess, and each socket having an internal thread connection formation adapted to mate with a counterpart external thread connection formation on the stopper of a corresponding vial to be connected thereto.

* * * * *